(12) United States Patent
Kaizik et al.

(10) Patent No.: US 7,524,997 B2
(45) Date of Patent: Apr. 28, 2009

(54) PROCESS FOR THE HYDROGENATION OF OXO ALDEHYDES HAVING HIGH ESTER CONTENTS

(75) Inventors: Alfred Kaizik, Marl (DE); Hans-Gerd Lüken, Marl (DE); Michael Grass, Haltern am See (DE); Dietrich Maschmeyer, Recklinghausen (DE); Wilfried Büschken, Haltern am See (DE)

(73) Assignee: OXENO Olefinchemie GmbH, Marl (DE)

( * ) Notice: Subject to any disclaimer, the term of this patent is extended or adjusted under 35 U.S.C. 154(b) by 0 days.

(21) Appl. No.: 11/494,741

(22) Filed: Jul. 28, 2006

(65) Prior Publication Data

US 2007/0027346 A1    Feb. 1, 2007

(30) Foreign Application Priority Data

Jul. 30, 2005    (DE) .................. 10 2005 035 816

(51) Int. Cl.
*C07C 29/141*    (2006.01)
*C07C 29/149*    (2006.01)
*B01J 23/75*    (2006.01)
*B01J 23/755*    (2006.01)

(52) U.S. Cl. .................. 568/883; 568/882; 568/881; 568/880; 502/326; 502/329; 502/330; 502/331; 502/340

(58) Field of Classification Search .................. 502/328, 502/329, 330, 331, 337, 345, 344, 343, 340; 568/883, 882, 881, 880
See application file for complete search history.

(56) References Cited

U.S. PATENT DOCUMENTS

| | | | |
|---|---|---|---|
| 2,809,220 A | 10/1957 | Mertzweiller et al. | |
| 4,401,834 A | 8/1983 | King | |
| 4,709,105 A | 11/1987 | Grenacher et al. | |
| 4,950,633 A | 8/1990 | Yamaguchi et al. | |
| 5,059,710 A | 10/1991 | Abatjoglou et al. | |
| 6,015,928 A | 1/2000 | Gubishc et al. | |
| 6,184,424 B1 | 2/2001 | Bueschken et al. | |
| 6,239,318 B1 | 5/2001 | Schuler et al. | |
| 6,331,657 B1 | 12/2001 | Kaizik et al. | |
| 6,332,976 B1 * | 12/2001 | Mignard et al. ............. | 208/217 |
| 6,403,836 B2 | 6/2002 | Kaizik et al. | |
| 6,407,295 B1 | 6/2002 | Kaizik et al. | |
| 6,482,992 B2 | 11/2002 | Scholz et al. | |
| 6,492,564 B1 | 12/2002 | Wiese et al. | |
| 6,500,991 B2 | 12/2002 | Wiese et al. | |
| 6,555,716 B2 | 4/2003 | Protzmann et al. | |
| 6,570,033 B2 | 5/2003 | Rottger et al. | |
| 6,627,782 B2 | 9/2003 | Kaizik et al. | |
| 6,680,414 B2 | 1/2004 | Knoop et al. | |
| 6,720,457 B2 | 4/2004 | Drees et al. | |
| 6,818,770 B2 | 11/2004 | Selent et al. | |
| 6,924,389 B2 | 8/2005 | Jackstell et al. | |
| 6,930,213 B1 | 8/2005 | Pompetzki et al. | |
| 6,956,133 B2 | 10/2005 | Jackstell et al. | |
| 6,960,699 B2 | 11/2005 | Totsch et al. | |
| 7,009,068 B2 | 3/2006 | Schmutzler et al. | |
| 7,022,645 B2 * | 4/2006 | Ryu et al. .................... | 502/328 |
| 7,109,346 B2 | 9/2006 | Beller et al. | |
| 2004/0236133 A1 | 11/2004 | Selent et al. | |
| 2004/0238787 A1 | 12/2004 | Wiese et al. | |
| 2004/0242947 A1 | 12/2004 | Beller et al. | |
| 2005/0043279 A1 | 2/2005 | Selent et al. | |
| 2005/0182277 A1 | 8/2005 | Totsch et al. | |
| 2005/0209489 A1 | 9/2005 | Moller et al. | |
| 2005/0234270 A1 | 10/2005 | Kaizik et al. | |
| 2005/0256281 A1 | 11/2005 | Grund et al. | |
| 2006/0036121 A1 | 2/2006 | Kaizik et al. | |
| 2006/0128998 A1 | 6/2006 | Lueken et al. | |
| 2006/0129004 A1 | 6/2006 | Lueken et al. | |
| 2006/0161017 A1 | 7/2006 | Grass et al. | |
| 2006/0183936 A1 | 8/2006 | Grass et al. | |
| 2006/0241324 A1 | 10/2006 | Moeller et al. | |
| 2007/0027346 A1 | 2/2007 | Kaizik et al. | |

FOREIGN PATENT DOCUMENTS

| | | |
|---|---|---|
| DE | 3542595 | 6/1987 |
| DE | 43 10 971 A1 | 10/1994 |
| DE | 19842370 | 3/2000 |
| DE | 199 33 348 A1 | 2/2001 |
| DE | 10062448 | 6/2002 |
| EP | 1 219 584 A2 | 7/2002 |
| GB | 2142010 | 1/1985 |
| GB | 2142010 A * | 1/1985 |

OTHER PUBLICATIONS

U.S. Appl. No. 11/494,741, filed Jul. 28, 2006, Kaizik, et al.

(Continued)

*Primary Examiner*—Elvis O Price
(74) *Attorney, Agent, or Firm*—Oblon, Spivak, McClelland, Maier & Neustadt, P.C.

(57) ABSTRACT

A hydrogenation catalyst is used for the catalytic hydrogenation of an ester-containing aldehyde mixture and the catalyst contains a γ-alumina having a BET surface area of from 70 to 350 $m^2/g$ as support material, and at least one component having hydrogenation activity and being selected from the group consisting of nickel, cobalt and mixtures thereof.

20 Claims, No Drawings

OTHER PUBLICATIONS

U.S. Appl. No. 10/562,454, filed Aug. 18, 2006, Krissmann, et al.
U.S. Appl. No. 10/576,302, filed Apr. 19, 2006, Kaizik, et al.
U.S. Appl. No. 10/588,762, filed Aug. 8, 2006, Wiese, et al.
U.S. Appl. No. 10/593,330, filed Sep. 19, 2006, Borgmann, et al.
U.S. Appl. No. 10/584,492, filed Jun. 22, 2006, Ortmann, et al.
U.S. Appl. No. 10/584,148, filed Jun. 22, 2006, Ortmann, et al.
U.S. Appl. No. 11/574,063, filed Feb. 22, 2007, Nierlich, et al.
U.S. Appl. No. 12/065,091, filed Feb. 28, 2008, Hess, et al.
J. Falbe, "New Syntheses with Carbon Monoxide", Springer-Verlag, Berlin Heidelberg-New York, 1980, p. 99 et seq.
Kirk-Othmer, Encyclopedia of Chemical Technology, vol. 17, 4th edition, John Wiley & Sons, pp. 902 to 919 (1996).
esp@cenet.com English Abstract of DE19842370.
esp@ cenet.com English Abstract of DE 3542595.
esp@cenet.com English Abstract of DE10062448.

* cited by examiner

PROCESS FOR THE HYDROGENATION OF OXO ALDEHYDES HAVING HIGH ESTER CONTENTS

BACKGROUND OF THE INVENTION

1. Field of the Invention

The present invention relates to a process for the preparation of alcohols by hydrogenating hydroformylation mixtures having high ester contents in the liquid phase, and catalysts for this purpose.

2. Description of the Related Art

Alcohols can be prepared by catalytic hydrogenation of aldehydes which have been obtained, for example, by hydroformylation of olefins. Large amounts of alcohols prepared, for example, in this manner are used as solvents and as intermediates for the preparation of many organic compounds. Important subsequent products of alcohols are plasticizers and detergents.

It is known that aldehydes can be reduced catalytically with hydrogen to give alcohols. Catalysts which contain at least one metal from the groups Ib, IIb, VIa, VIIa, and/or VIIIa of the Periodic Table of the Elements are frequently used for this purpose. The hydrogenation of aldehydes can be carried out continuously or batchwise in the gas or liquid phase using catalysts in the form of powder or pieces.

For the industrial production of alcohols by hydrogenation of aldehydes from the oxo process (hydroformylation of olefins), especially in the case of mass-produced products, continuous processes using catalysts arranged in a fixed bed in the gas or liquid phase are preferred.

In comparison with the gas-phase hydrogenation, the liquid-phase hydrogenation has the more favorable energy balance and the higher space-time yield. With increasing molar mass of the aldehyde to be hydrogenated, i.e. with increasing boiling points, the advantage of the more favorable energy balance increases. Higher aldehydes having more than 7 carbon atoms are accordingly preferably hydrogenated in the liquid phase.

The hydrogenation in the liquid phase has, however, the disadvantage that, owing to the high concentrations of both aldehydes and alcohols, the formation of high boilers due to subsequent and secondary reactions is promoted. Thus, aldehydes can more readily undergo aldol reactions (addition and/or condensation) and form hemiacetals or full acetals with alcohols. With elimination of water or alcohol, the resulting acetals can form enol ethers, which are hydrogenated under the reaction conditions to give the saturated ethers. As a result of formation of these secondary byproducts, the yield is reduced. The byproducts designated as high boilers can at best be partly cleaved in downstream plants to give desired products, such as starting aldehydes and target alcohols.

Industrial aldehyde mixtures which are used for the hydrogenation frequently already contain high boilers in different concentration.

The hydroformylation of olefins in the presence of cobalt and rhodium catalysts gives crude aldehydes which, in addition to aldol products, ethers and acetals, also contain esters, in particular formic esters (formates), as high boilers. If these mixtures are hydrogenated in the gas phase, the major part of the high boilers can be separated off in the evaporator and worked up in a separate process step to give desired products.

In the liquid-phase hydrogenation, on the other hand, the high boilers remain in the reactor feed. They are hydrogenated in the hydrogenation stage for the most part to products from which a desired product can no longer be obtained. Esters present in the reactor feed are frequently not converted into the corresponding target alcohols.

In U.S. Pat. No. 5,059,710, the yield of alcohols obtained by hydrogenation of crude aldehydes is increased by cleaving, in a process stage upstream of the hydrogenation, a part of the high boilers at elevated temperature with water to give aldehydes or alcohols. Hydrolysis and hydrogenation are therefore separate process stages, the document giving no information about the water content of the mixture to be hydrogenated.

A similar process is disclosed in U.S. Pat. No. 4,401,834. Here too, the cleavage of high boilers is effected in the presence of water before the actual hydrogenation step.

GB 2 142 010 claims a process for the hydrogenation of crude aldehydes having 6 to 20 C atoms, which contain high boilers and small amounts of sulfur compounds, to give the corresponding saturated alcohols. The hydrogenation is effected in two reactors connected in series. The first reactor contains an $MoS_2/C$ catalyst and the second reactor an $Ni/Al_2O_3$ catalyst. The hydrogenation is carried out in both reactors with addition of up to 10% of steam, based on the starting material stream, in the temperature range of from 180 to 260° C. and at a hydrogen partial pressure of from 15 to 21 MPa with a large excess of hydrogen. According to the examples, this is so large that the water added is present virtually only in the gas phase. The object of this process is to suppress the formation of hydrocarbons by hydrogenolysis of the alcohols. No information is given concerning an increase or decrease of high boilers and formates in the hydrogenation.

In U.S. Pat. No. 2,809,220, a liquid-phase hydrogenation of hydroformylation mixtures in the presence of water is described. Sulfur-containing catalysts are used as the catalyst. The hydrogenation is carried out in the pressure range of from 10.5 to 31.5 MPa and in the temperature range of from 204 to 315° C. in the presence of from 1 to 10% of water, based on the starting material. In order to keep the added water in the gas phase, a large excess of hydrogen (from 892 to 3566 $Nm^3$ of hydrogen per $m^3$ of starting material) is used. Regarding the large hydrogen excess, reference is made to the discussion in GB 2 142 010. Furthermore, the high specific energy consumption is disadvantageous in this process.

A further process for the hydrogenation of hydroformylation mixtures is disclosed in DE 198 42 370. This describes how hydroformylation mixtures can be hydrogenated in the liquid phase over copper-, nickel- and chromium-containing supported catalysts. Depending on the process for the preparation of the hydroformylation mixtures (rhodium or cobalt process) these mixtures contain water. The process disclosed is designed for the selective hydrogenation of the aldehydes to alcohols, without hydrogenation of the olefins not converted in the hydroformylation, i.e. the high boilers (especially acetals) are not converted into desired product. This is economically disadvantageous and therefore capable of improvement.

DE 100 62 448 describes a process for the hydrogenation of aldehydes having ester contents of up to 5% by mass to give the corresponding alcohols. The hydrogenation is carried out in the liquid phase in the presence of homogeneously dissolved water. The catalysts used are preferably copper-containing supported catalysts. In this process, aldehydes are hydrogenated to the corresponding alcohols virtually without formation of high boilers. However, there is the disadvantage that the esters are converted only slowly into the corresponding alcohols, so that, with high selectivity, only a low space-time yield results.

DE 35 42 595 describes a two-stage hydrogenation process for the hydrogenation of ester-containing hydroformylation mixtures. There, a supported catalyst comprising silica as a support and nickel and molybdenum as components having hydrogenation activity is used in the first hydrogenation stage, and a catalyst which contains the metals cobalt, copper, manganese and molybdenum having hydrogenation activity is used in the second stage. The main disadvantage of this process is that hydrogenation pressures of 25 MPa are used in order to obtain good yields.

SUMMARY OF THE INVENTION

Since the known hydrogenation processes are not cost-efficient (i.e. do not result in low capital costs, high product yield, high space-time yield, low energy consumption) for the conversion of aldehyde mixtures having high ester contents into the corresponding alcohols, it is an object of the present invention to provide a hydrogenation process which fulfills the above requirements.

This and other objects have been achieved by the present invention the first embodiment of which includes a hydrogenation catalyst, comprising:

a γ-alumina having a BET surface area of from 70 to 350 $m^2/g$ as support material, and at least one component having hydrogenation activity and being selected from the group consisting of nickel, cobalt and mixtures thereof.

In another embodiment, the present invention relates to a process for the catalytic hydrogenation of an ester-containing aldehyde mixture, comprising:

hydrogenating said ester-containing aldehyde in the presence of a supported catalyst, thereby obtaining at least one alcohol corresponding to said aldehyde, wherein said supported catalyst comprises γ-alumina having a BET surface area of from 70 to 350 $m^2/g$ as support material and at least one component having hydrogenation activity and being selected from the group consisting of nickel, cobalt and mixtures thereof.

DETAILED DESCRIPTION OF THE INVENTION

It was surprisingly found that supported catalysts comprising γ-alumina as a support, which has a BET surface area of from 70 to 350 $m^2/g$, and nickel or cobalt or a combination thereof as the metal having hydrogenation activity are outstandingly suitable for the hydrogenation of ester-containing aldehydes to the corresponding alcohols. The catalysts according to the present invention hydrogenate the starting materials with high selectivity and with high space-time yield to give the corresponding alcohols. This was very surprising since it is known that secondary reactions take place in particular over nickel catalysts, for example ether formation or over-hydrogenation of the target alcohols to give the corresponding alkanes.

The present invention therefore relates to a hydrogenation catalyst which has a γ-alumina having a BET surface area of from 70 to 350 $m^2/g$ as support material and nickel and/or cobalt as a component having hydrogenation activity. The BET surface area includes all values and subvalues therebetween, especially including 80, 100, 120, 140, 160, 180, 200, 220, 240, 260, 280, 300, 320 and 340 $m^2/g$.

The present invention also relates to a process for the catalytic hydrogenation of aldehydes in ester-containing aldehyde mixtures to give the corresponding alcohols, wherein a supported catalyst which has γ-alumina having a BET surface area of from 70 to 350 $m^2/g$ as support material and nickel and/or cobalt as a component having hydrogenation activity is used. The BET surface area includes all values and subvalues therebetween, especially including 80, 100, 120, 140, 160, 180, 200, 220, 240, 260, 280, 300, 320 and 340 $m^2/g$.

The process according to the present invention for the hydrogenation of ester-containing aldehyde mixtures, which form in particular in the hydroformylation of olefins, to give the corresponding alcohols, in which the catalyst according to the present invention is used has a number of advantages. For example, the selectivity of the alcohol formation in the process according to the present invention is high. Moreover, scarcely any high boilers form in the process according to the present invention, for example as a result of acetal formation, aldol addition, aldol condensation and subsequent reactions. In the process according to the present invention, both the aldehydes and the esters are converted into the corresponding alcohols with high space-time yields. In contrast to known processes, the process according to the present invention can be carried out at relatively low pressures.

The present invention is described by way of example below without there being any intention of limiting the present invention thereto, the scope of protection of which is evident from the claims and the entire description. The claims themselves are also part of the disclosure content of the present invention. Where ranges or preferred ranges are stated in the text below, all theoretically possible partial ranges present in these ranges are also intended to be part of the disclosure content of the present invention without these having been explicitly mentioned, for the sake of greater clarity.

The hydrogenation catalyst according to the present invention, which is preferably used for the hydrogenation of ester-containing aldehyde mixtures, is distinguished in that it has a γ-alumina having a BET surface area of from 70 to 350 $m^2/g$, preferably from 110 to 250 $m^2/g$ (determined according to the BET method by nitrogen adsorption according to DIN ISO 9277) as support material, and nickel and/or cobalt as the component having hydrogenation activity. The mean pore volume (determined by mercury porosimetry according to DIN 66133) is preferably from 0.5 to 0.8 $cm^3/g$. The mean pore volume includes all values and subvalues therebetween, especially including 0.55, 0.6, 0.65, 0.7 and 0.75 $cm^3/g$.

The compositions stated below are based on the reduced catalysts. The catalysts according to the present invention preferably contains from 5 to 30% by mass of nickel (calculated as metal) and/or from 5 to 30% by mass of cobalt (calculated as metal), preferably from 15 to 25% by mass of nickel and/or from 15 to 25% by mass of cobalt. The catalyst according to the present invention preferably contains from 17.5 to 22.5% by mass of cobalt. Although the esters are also degraded by means of catalysts which comprise from 17.5 to 22.5% by mass of nickel in a similarly good manner compared with the cobalt catalyst, lower yields of alcohol may result with decreasing concentration of esters if the hydrogenation is carried out for a long time at low ester concentrations. The amount of nickel and/or cobalt includes all values and subvalues therebetween, especially including 6, 8, 10, 12, 14, 16, 18, 20, 22, 24, 26 and 28% by mass. The catalysts according to the present invention are preferably free of copper or noble metals, in particular free of Cu, Ru, Rh, Pd, Ag, Au, Pt, Ir and/or Os.

Optionally, the catalysts according to the present invention may contain alkali metal, alkaline earth metal or zinc compounds. The proportion of these compounds (calculated as metal oxide) is preferably from 0.01 to 3% by mass, preferably from 0.05 to 1% by mass. The proportion of the above compounds includes all values and subvalues therebetween, especially including 0.05, 0.1, 0.5, 1, 1.5, 2 and 2.5% by mass.

Furthermore, the catalysts can optionally contain processing auxiliaries, such as, for example, graphite.

The catalysts according to the present invention can be prepared by applying at least one metal selected from cobalt or nickel to a suitable γ-alumina. Suitable support material is obtainable, for example, under the trade names SP E538 from Axens and Alcoa LD 350 from Alcoa. Suitable support materials which are preferably used are those which have a mean pore volume of from 0.5 to 0.8 cm$^3$/g. The mean pore volume includes all values and subvalues therebetween, especially including 0.55, 0.6, 0.65, 0.7 and 0.75 cm$^3$/g. The application of the at least one metal can be effected by treatment of the support with suitable metal compounds themselves, with a solution or dispersion of metal compounds or with metal salt solutions, in particular aqueous metal salt solutions, of the corresponding metals. Treatment can be effected, for example, by impregnation of the support in or with one of said solutions or dispersions or by spraying of the support with one of said solutions or dispersions or by other suitable methods. Suitable metal compounds are, for example, nitrates, halides, carbonates, carboxylates and acetylacetonates of the metals and the soluble metal complexes thereof, for example amine complexes. For example, alcohols or water may be used as optionally present solvent. Water is used as a preferred solvent. If it is intended to prepare catalysts in which more than one metal is applied, the corresponding metal compounds can be applied simultaneously or in succession.

The amount of metal compounds used or the amount and concentration of the solutions or dispersions of metal compounds used, in particular of metal salts, are in each case such that the desired proportion by mass of the component having hydrogenation activity is reached in the catalyst.

The supports treated, i.e. in particular coated or impregnated, with a metal compound or a solution or dispersion of a metal compound, in particular a metal salt solution, are then preferably calcined at a temperature of from 200 to 600° C. The calcinations temperature includes all values and subvalues therebetween, especially including 250, 300, 350, 400, 450, 500 and 550° C. It may be advantageous if the treated support is first dried before the calcination. The drying is preferably effected at a temperature of from 80 to 150° C. The drying temperature includes all values and subvalues therebetween, especially including 90, 100, 110, 120, 130 and 140° C. If the treatment of the support is effected in a plurality of steps, for example by impregnating or spraying several times, it may be advantageous if a drying step and/or calcination step as described above is carried out after each treatment step. If not just one component having hydrogenation activity is applied to the support the sequence in which the components having hydrogenation activity are applied can be freely chosen.

Optionally, the application of the components having hydrogenation activity, drying and calcination can be effected in one operation, for example by spraying an aqueous metal salt solution onto the support at temperatures above 200° C.

The catalysts according to the present invention are preferably brought into a form which offers lower resistance to flow during the subsequent use, for example in the hydrogenation, such as, for example, tablets, cylinders, extrudates or rings. The shaping can optionally be effected at various points in the catalyst preparation, in particular before or after the calcination.

The process according to the present invention for the catalytic hydrogenation of ester-containing aldehyde mixtures to give the corresponding alcohols is distinguished in that a supported catalyst which has γ-alumina having a BET surface area of from 70 to 350 m$^2$/g, preferably from 110 to 250 m$^2$/g, is used as supporting material, and nickel and/or cobalt is used as the component having hydrogenation activity.

Particularly preferably, the above-described catalyst according to the present invention is used in the process according to the present invention. The catalyst used preferably contains from 5 to 30% by mass of nickel and/or from 5 to 30% by mass of cobalt and particularly preferably from 15 to 25% by mass of nickel and/or from 15 to 25% by mass of cobalt based on the total mass of the reduced catalyst. The amount of nickel and/or cobalt includes all values and subvalues therebetween, especially including 6, 8, 10, 12, 14, 16, 18, 20, 22, 24, 26 and 28% by mass. In addition to these components, the catalyst can contain further components used according to the present invention. The support material preferably has a mean pore volume of from 0.5 to 0.8 cm$^3$/g. The mean pore volume includes all values and subvalues therebetween, especially including 0.55, 0.6, 0.65, 0.7 and 0.75 cm$^3$/g.

In the process according to the present invention, the hydrogenation can be carried out over suspended catalysts or catalysts in the form of pieces which are arranged in a fixed bed, continuously or batchwise. In the process according to the present invention, a continuous hydrogenation over a catalyst arranged in a fixed bed, in which the product/starting material phase is present mainly in the liquid state under reaction conditions, is preferably carried out.

If the hydrogenation is carried out continuously over a catalyst arranged in a fixed bed, it is expedient to convert the catalyst into the active form before the hydrogenation. This can be effected by reduction of the catalyst with hydrogen-containing gasses according to a temperature program. The reduction can optionally be carried out in the presence of a liquid phase which trickles over the catalyst. A solvent or the hydrogenation product can be used as the liquid phase.

Different process variants can be chosen for the process according to the present invention. It can be carried out adiabatically, polytropically or virtually isothermally, i.e. with a temperature increase of, typically, less than 10° C., in one or more stages. In the latter case, all reactors, preferably tubular reactors, can be operated adiabatically or virtually isothermally and one or more adiabatically and the others virtually isothermally. It is furthermore possible to carry out the hydrogenation in one, in a plurality or in all of the reactors used, in a straight pass or with product recycling.

The process according to the present invention is preferably carried out in the mixed liquid/gas phase or liquid phase in three-phase reactors by the cocurrent method, the hydrogenation gas being distributed in a manner known per se in the liquid starting material/product stream. In the interests of uniform liquid distribution, of improved removal of the heat of reaction and of a high space-time yield, the reactors are preferably operated with high liquid loads of from 15 to 120, preferably from 25 to 80 m$^3$ per m$^2$ cross section of the empty reactor per hour. If a reactor is operating in a straight pass, the specific catalyst loading (LHSV) may assume values of from 0.1 to 10 h$^{-1}$. The liquid load includes all values and subvalues therebetween, especially including 20, 25, 30, 35, 40, 45, 50, 55, 60, 65, 70, 75, 80, 85, 90, 95, 100, 105, 110, and 115 m$^3$ per m$^2$ cross section of the empty reactor per hour. The LHSV includes all values and subvalues therebetween, especially including 0.5, 1, 1.5, 2, 2.5, 3, 3.5, 4, 4.5, 5, 5.5, 6, 6.5, 7, 7.5, 8, 8.5, 9, 9.5 h$^{-1}$.

The hydrogenation can be carried out without or preferably with a solvent. Solvents which may be used are all liquids which form a homogeneous solution with the starting material and product, are inert under hydrogenation conditions and can easily be separated from the product. The solvent may also be a mixture of a plurality of substances and may optionally contain water.

For example, the following substances can be used as solvents:

Straight-chain or cyclic ethers, such as, for example, tetrahydrofuran or dioxane, and aliphatic alcohols in which the alkyl radical has 1 to 13 carbon atoms. Alcohols which may preferably be used are isopropanol, n-butanol, isobutanol, n-pentanol, 2-ethylhexanol, nonanols, industrial nonanol mixtures, decanol, industrial decanol mixtures and tridecanols. A further preferred solvent is the hydrogenation product itself.

By using a solvent, it is possible to limit the aldehyde concentration in the reactor feed, with the result that better temperature control in the reactor can be achieved. This may result in a minimization of secondary reactions and hence an increase in the product yield. The aldehyde content in the reactor feed is preferably from 1 to 35%, particularly preferably from 5 to 25%. The aldehyde content includes all values and subvalues therebetween, especially including 5, 10, 15, 20, 25 and 30% by weight. In the case of reactors which are operated by the loop procedure, the desired concentration range can be adjusted by means of the circulation ratio (ratio of recycled hydrogenation discharge to starting material).

The hydrogenation according to the present invention can be carried out without addition of water to the ester-containing aldehyde mixture. Preferably, however, the hydrogenation according to the present invention is carried out with addition of water to the ester-containing aldehyde mixture. The hydrogenation can be carried out in the presence of water, for example as described in DE 100 62 448. The hydrogenation is preferably effected with addition of water so that, in the hydrogenation discharge, from 0.05 to 10% by mass of water is dissolved in the liquid hydrogenation discharge. The amount of water includes all values and subvalues therebetween, especially including 0.1, 0.5, 1, 1.5, 2, 2.5, 3, 3.5, 4, 4.5, 5, 5.5, 6, 6.5, 7, 7.5, 8, 8.5, 9 and 9.5% by mass.

The process according to the present invention is preferably carried out at a pressure of from 0.5 to 25 MPa, preferably from 1 to 15 MPa and particularly preferably from 1.5 to 3 MPa. The pressure includes all values and subvalues therebetween, especially including 1, 2, 4, 6, 8, 10, 12, 14, 16, 18, 20, 22 and 24 MPa. Preferably, the process according to the present invention is carried out at a temperature from 120 to 220° C., preferably from 140 to 210° C. and particularly preferably from 160 to 190° C. The temperature includes all values and subvalues therebetween, especially including 130, 140, 150, 160, 170, 180, 190, 200 and 210 ° C.

Any desired hydrogen-containing gas mixtures, which preferably contain no harmful amounts of catalyst poisons, such as, for example, carbon monoxide or hydrogen sulfide, can be used as hydrogenation gases. The use of inert gases is optional; pure hydrogen or hydrogen having a purity greater than 95%, particularly greater than 98%, is preferably used. Inert gas constituents may be, for example, nitrogen or methane. The purity includes all values and subvalues therebetween, especially including 95.5, 96, 96.5, 97, 97.5, 98, 98.5, 99, 99.5, 99.9 and 100%.

It may be advantageous if the individual reactors are fed with fresh hydrogen. In order to minimize the hydrogen consumption and the discharge losses caused by the exit gas, it is, however, expedient to use the exit gas of a reactor as hydrogenation gas of another reactor. For example, in a process which is carried out in two reactors connected in series, it is advantageous to feed fresh hydrogen into the second reactor and to pass the exit gas of the second reactor into the first reactor. In this case, feedstock and hydrogenation gas flow in the opposite sequence through the reactors. It is preferable to keep the excess of hydrogen, based on the stoichiometrically required amount (taking into account the conversion strived for) below 30%, in particular below 10%, very particularly below 5%. The excess of hydrogen includes all values and subvalues therebetween, especially including 25, 20, 15, 10, 5, 4, 3, 2, 1, 0.5, 0.1 and 0.01%.

With the aid of the process according to the present invention, saturated or olefinically unsaturated aldehydes can be hydrogenated to give the corresponding saturated alcohols. Aldehydes or aldehyde mixtures which were obtained by a very wide range of processes, for example by aldol condensation, can be used here. In particular, however, aldehyde mixtures which were obtained by hydroformylation of olefins are used. These hydroformylation mixtures also contain esters, in particular formates, in addition to the aldehydes. In the hydroformylation of olefins or olefin mixtures having 8 to 16 C atoms and a degree of branching (average number of branches, n-olefins having a degree of branching of 0) of more than 1, the ester contents in the hydroformylation mixture can assume values of up to 30% by mass at conversions of more than 80%. A preferably used ester-containing aldehyde mixture is a reaction mixture from the hydroformylation of olefins having 6 to 20 C atoms, which has an ester content of from 1 to 25% by mass, particularly preferably from 3 to 15% by mass and very particularly preferably from 5 to 10% by mass. The ester content includes all values and subvalues therebetween, especially including 2, 4, 6, 8, 10, 12, 14, 16, 18, 20, 22 and 24% by mass.

Starting materials for the preparation of the ester-containing aldehyde mixtures by hydroformylation may be, for example, olefins having 6 to 20 C atoms, preferably 8 to 20 C atoms, with terminal or internal olefinic double bonds, such as, for example, 1-, 2- or 3-hexene, the $C_6$-olefin mixture (dipropene) obtained in the dimerization of propene, heptenes, 2- or 3-methyl-1-hexene, octenes, 2-methylheptenes, 3-methylheptenes, 5-methylhept-2-ene, 6-methylhept-2-ene, 2-ethylhex-1-ene, the mixture of isomeric $C_8$ olefins (dibutene) obtained in the dimerization of butenes, nonenes, 2- or 3-methyloctenes, the $C_9$-olefin mixture (tripropene) obtained in the trimerization of propene, decenes, 2-ethyl-1-octene, dodecenes, the $C_{12}$ olefin mixture (tetrapropene or tributene) obtained in the tetramerization of propene or the trimerization of butenes, tetradecenes, pentadecenes, hexadecenes, the $C_{16}$ olefin mixture (tetrabutene) obtained in the tetramerization of butenes, the $C_{20}$ olefin mixture (pentabutene) obtained in the pentamerization of butenes, and olefin mixtures prepared by cooligomerization of olefins having different numbers of carbon atoms (preferably from 2 to 4), optionally after distillative separation into fractions having identical or similar chain lengths. Olefins or olefin mixtures which have been produced by Fischer Tropsch synthesis and olefins which were obtained by oligomerization of ethene or olefins which are obtainable via metathesis reactions can also be used. Preferred starting materials for the preparation of the hydroformylation mixtures are $C_8$-, $C_9$-, $C_{12}$-, $C_{15}$-, $C_{16}$- or $C_{20}$-olefin mixtures.

The olefins can be hydroformylated in a customary manner. The reaction mixtures of the hydroformylation can then be used as starting materials for the hydrogenation process according to the present invention. The hydroformylation can be effected using rhodium or cobalt catalysts with or without complex-stabilizing additive(s), such as organic phosphines or phosphites. The temperatures and pressures may vary within wide limits, depending on catalyst of olefin. A description of the hydroformylation of olefins is to be found, for example, in J. Falbe, New Syntheses with Carbon Monoxide, Springer-Verlag, Heidelberg-New York, 1980, page 99 et seq., and in Kirk-Othmer, Encyclopedia of Chemical Technology, volume 17, 4$^{th}$ edition, John Wiley & Sons, pages 902 to 919 (1996).

In the process according to the present invention, reaction mixtures from the hydroformylation of olefins having 8 to 18 C atoms, in particular hydroformylation mixtures prepared from $C_8$-, $C_{12}$- and $C_{16}$-olefins or $C_8$-, $C_{12}$- and $C_{16}$-olefin mixtures, are preferably hydrogenated as aldehyde mixtures. In the process according to the present invention, reaction mixtures from the hydroformylation of di-n-butene, tri-n-butene and tetra-n-butene are particularly preferably hydrogenated as aldehyde mixtures.

The reaction mixtures of the hydroformylation are preferably first freed from the catalyst before being used in the process according to the present invention. If a cobalt catalyst has been used, this can be effected by relieving the pressure, oxidizing the cobalt carbonyl compounds remaining in the hydroformylation mixture in the presence of water or aqueous acid and separating off the aqueous phase. Cobalt removal methods are well known, cf. for example J. Falbe, in "New Syntheses with Carbon Monoxide", Springer Verlag (1980), Berlin, Heidelberg, New York, page 158 et seq.

The reaction mixtures freed from the hydroformylation catalyst may contain from 3 to 40% by mass, preferably from 5 to 30% by mass, of low boilers, depending on the catalyst system used for the hydroformylation. The amount of low boilers includes all values and subvalues therebetween, especially including 4, 6, 8, 10, 12, 14, 16, 18, 20, 22, 24, 26, 28, 30, 32, 34, 36 and 38% by mass. These low boilers may comprise mainly unconverted olefins, additionally the corresponding saturated hydrocarbons and from 0.05 to 5% by mass of water, from 30 to 90% by mass of aldehydes, from 5 to 60% by mass of alcohols, from 0.5 to 30% by mass of esters, mainly formates of these alcohols, and from 0.5 to 15% by mass of high boilers. The amount of water includes all values and subvalues therebetween, especially including 0.1, 0.5, 1, 1.5, 2, 2.5, 3, 3.5, 4 and 4.5% by mass. The amount of aldehyde includes all values and subvalues therebetween, especially including 35, 40, 45, 50, 55, 60, 65, 70, 75, 80 and 85% by mass. The amount of alcohol includes all values and subvalues therebetween, especially including 10, 15, 20, 25, 30, 35, 40, 45, 50 and 55% by mass. The amount of the formate includes all values and subvalues therebetween, especially including 1, 5, 10, 15, 20, and 25% by mass. The amount of high boilers includes all values and subvalues therebetween, especially including 1, 5, and 10% by mass.

However, it should be emphasized that the process according to the present invention can also be carried out using hydroformylation mixtures whose composition does not correspond to these data in this and/or that respect. Thus, for example, the hydrocarbons (olefins and paraffins) can be separated from the hydroformylation mixture before the hydrogenation.

The hydrogenation product obtained by the process according to the present invention can be worked up by distillation. This can be effected at atmospheric pressure or reduced pressure. In the case of high-boiling alcohols (alcohols having more than 9 carbon atoms), the distillation at reduced pressure is preferred. Optionally, the alcohol obtained is separated into a plurality of fractions.

The alcohols obtained by the process according to the present invention can be used, for example, for the preparation of plasticizers or detergents.

Having generally described this invention, a further understanding can be obtained by reference to certain specific examples which are provided herein for purposes of illustration only, and are not intended to be limiting unless otherwise specified.

EXAMPLES

Example 1

Comparative Example $C_{13}$-aldehyde hydrogenation in the liquid phase at 2.5 MPa/Cu—Cr—Ni-catalyst (H14279, supplier: Degussa, Düsseldorf)

One liter of a reaction discharge of the Rh-catalyzed hydroformylation of tributene comprising 15.42% by mass of $C_{13}$-aldehyde and 9.13% by mass of esters was hydrogenated in a circulation apparatus at 180° C. and 2.5 MPa absolute over 100 g of a Cu/Cr/Ni catalyst (6.7% by mass of Cu, 3% by mass of Ni and 0.7% by mass of Cr) on a γ-$Al_2O_3$ support in the liquid phase. The amount of exit gas was 1 l(FTP)/h. The analyses of starting material and product, which were effected by gas chromatography, are reproduced in Table 1.

TABLE 1

| Test time (hours) | $C_{12}$-hydrocarbon (% by mass) | $C_{13}$-al (% by mass) | Formate (% by mass) | $C_{13}$-ol (% by mass) | High boilers (% by mass) |
|---|---|---|---|---|---|
| 0 | 8.35 | 15.42 | 9.13 | 66.95 | 0.15 |
| 0.5 | 8.61 | 4.21 | 7.44 | 79.54 | 0.20 |
| 1 | 8.64 | 2.74 | 7.23 | 81.17 | 0.22 |
| 3 | 8.72 | 1.76 | 5.40 | 83.45 | 0.67 |

As can be seen from Table 1, the esters are cleaved only with moderate yield to give the desired product isotridecanol in the hydrogenation of isotridecanal.

Example 2

Comparative Example $C_{13}$-aldehyde hydrogenation at 6 MPa/Cu—Cr—Ni catalyst (H14279); supplier: Degussa, Düsseldorf)

One liter of a reaction discharge of the Rh catalyzed hydroformylation of tributene comprising 15.82% by mass of $C_{13}$-aldehyde and 9.53% by mass of esters was hydrogenated in a circulation apparatus at 180° C. and 6 MPa absolute over 100 g of a Cu/Cr/Ni catalyst on γ-$Al_2O_3$ support (for composition cf. comparative example 1) in the liquid phase. The amount of exit gas was 1 l(S.T.P.)/h. The analyses of starting material and product are reproduced in Table 2.

TABLE 2

| Test time (hours) | $C_{12}$-hydrocarbon (% by mass) | $C_{13}$-al (% by mass) | Formate (% by mass) | $C_{13}$-ol (% by mass) | High boilers (% by mass) |
|---|---|---|---|---|---|
| 0 | 8.20 | 15.82 | 9.53 | 66.25 | 0.20 |
| 0.5 | 8.93 | 2.87 | 4.37 | 82.90 | 0.93 |
| 1 | 8.75 | 2.45 | 3.04 | 84.36 | 1.40 |
| 3 | 8.85 | 1.65 | 1.16 | 86.69 | 1.65 |

As can be seen from Table 2, esters (formates) are cleaved substantially more rapidly to give desired products by controlled increase of the reaction pressure from 2.5 to 6 MPa.

Example 3

Preparation of Supported Nickel Catalysts (According to the Invention)

A commercial alumina support (SP E538 from Axens) in the form of cylindrical extrudates having a diameter of about 1.2 mm and a length of from 4 to 6 mm, which had a BET surface area of 270 m$^2$/g (determined by the BET method by nitrogen adsorption according to DIN ISO 9277) and a pore volume of 0.7 ml/g (determined by mercury porosimetry according to DIN 66133), was impregnated with an aqueous Co salt solution.

For the determination of the BET surface area, the alumina support was heated under reduced pressure at 200° C. to a residual pressure of less than 66 MPa. Using an ASAP 2400 sorption apparatus from Micromeritics, the adsorption isotherm of the degassed sample was recorded volumetrically with discontinuous supply of nitrogen. The evaluation was effected by multipoint determination. Nitrogen having a purity of 99.996% was used as the adsorptive. For the determination of the pore volume by means of Hg porosimetry, an apparatus of the type Pascal 140/440 from Porotec was used.

The catalyst support was impregnated twice with an aqueous hexamminenickel(II) carbonate solution whose nickel content was 18% by mass. The volume of solution absorbed by the support in the first impregnation process corresponded approximately to the pore volume of the support used. After the first impregnation, the impregnated support was dried in air at 120° C. for 12 h and then impregnated again with the aqueous hexamminenickel(II) carbonate solution. In the second impregnation process, the material absorbed only about 80% of the pore volume of the support. After drying for twelve hours at 120° C. in air, the catalyst was activated (reduced) at 450° C. for 16 h in a nitrogen/hydrogen mixture whose hydrogen content was increased stepwise from 5 to 50% by volume. After cooling to room temperature in an inert gas stream, the now pyrophoric catalyst was filled under tridecanol (hydrogenation product). The catalyst thus prepared contained 21% by mass of nickel, based on the mass of the reduced catalyst.

Example 4

Preparation of Supported Cobalt Catalysts (According to the Invention)

A commercial alumina support (SP E538 from Axens) in the form of extrudates having a diameter of about 1.6 mm and a length of from 4 to 6 mm, which had a BET surface area of 270 m$^2$/g (determined by the BET method by nitrogen adsorption according to DIN ISO 9277 as described in example 3) and a pore volume of 0.7 ml/g (determined by mercury porosimetry according to DIN 66133 as described in example 3), was impregnated with an aqueous cobalt(II) nitrate solution having a cobalt content of 22% by mass. The volume of the solution absorbed during the impregnation of the support corresponded approximately to the pore volume of the support used. Thereafter, the support impregnated with cobalt(II) nitrate solution was dried at 120° C. for 12 h and calcined in air, initially at 300° C. The catalyst was then activated (reduced) at 450° C. in a nitrogen/hydrogen mixture whose hydrogen content was increased stepwise from 5 to 50% by volume. After cooling to room temperature, the now pyrophoric catalyst was filled under tridecanol (hydrogenation product). The catalyst prepared in this way contained 18.5% by mass of cobalt, based on the mass of the reduced catalyst.

Example 5

According to the Invention $C_{13}$-aldehyde hydrogenation at 2.5 MPa/cobalt catalyst according to example 4

One liter of a reaction discharge of the Rh-catalysed hydroformylation of tributene comprising 15.89% by mass of $C_{13}$-aldehyde and 9.83% by mass of esters was hydrogenated in a circulation apparatus at 180° C. and 2.5 MPa absolute over 100 g of the Co catalyst on a γ-$Al_2O_3$ support, comprising 18.5% by mass of Co, according to example 4, in the liquid phase. The amount of exit gas was 1 l(S.T.P.)/h. The analyses of starting material and product are reproduced in Table 3.

TABLE 3

| Test time (hours) | $C_{12}$-hydrocarbon (% by mass) | $C_{13}$-al (% by mass) | Formate (% by mass) | $C_{13}$-ol (% by mass) | High boilers (% by mass) |
|---|---|---|---|---|---|
| 0 | 8.10 | 15.89 | 9.83 | 66.21 | 0.18 |
| 0.5 | 8.05 | 2.90 | 3.01 | 85.79 | 0.25 |
| 1 | 8.18 | 1.34 | 0.51 | 89.62 | 0.35 |
| 3 | 8.17 | 0.93 | 0.30 | 89.92 | 0.68 |

As can be seen from Table 3, the isotridecanyl formates are degraded very rapidly and selectively to the desired product isotridecanol in the hydrogenation of isotridecanal in the presence of the cobalt catalyst. In comparison with the Cu/Cr/Ni standard catalyst (c.f. examples 1 and 2), substantially higher yields are obtained in the presence of the Co catalyst according to the invention.

Example 6

According to the Invention $C_{13}$-aldehyde hydrogenation at 2.5 MPa/nickel catalyst according to example 3 One liter of a reaction discharge of the Rh catalysed hydroformylation of tributene comprising 14.54% by mass of $C_{13}$-aldehyde and 10.70% by mass of esters was hydrogenated in a circulation apparatus at 180° C. and 2.5 MPa absolute over 100 g of the nickel catalyst on a γ-$Al_2O_3$ support according to example 3, comprising 21% by mass of Ni, in the liquid phase. The amount of exit gas was 1 l(S.T.P.)/h. The analyses of starting material and product are reproduced in Table 4.

TABLE 4

| Test time (hours) | $C_{12}$-hydrocarbon (% by mass) | $C_{13}$-al (% by mass) | Formate (% by mass) | $C_{13}$-ol (% by mass) | High boilers (% by mass) |
|---|---|---|---|---|---|
| 0 | 8.28 | 14.54 | 10.70 | 66.29 | 0.19 |
| 0.5 | 8.43* | 2.15 | 0.68 | 88.49 | 0.25 |
| 1 | 8.55* | 1.18 | 0.53 | 89.39 | 0.35 |
| 3 | 9.93* | 1.11 | 0.23 | 88.28 | 0.45 |

*including $C_{13}$-hydrocarbon

As can be seen from Table 4, the isotridecanyl formates are degraded very rapidly to the desired product isotridecanol in the hydrogenation of isotridecanal also in the presence of a nickel catalyst. In contrast to the cobalt catalyst, the hydrogenation over the nickel catalyst must be terminated at the right time in order to avoid reducing the yield by further reaction.

German patent application 10 2005 035 816.0 filed Jul. 30, 2005, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A hydrogenation catalyst, comprising:
    a γ-alumina having a BET surface area of from 140 to 350 $m^2/g$ as only support material, and
    15 to 25% by mass of at least one component having hydrogenation activity, based on the total mass of the reduced catalyst,
    wherein said component having hydrogenation activity is selected from the group consisting of nickel, cobalt and mixtures thereof.

2. The catalyst as claimed in claim 1, wherein the BET surface area of the support material is from 140 to 250 $m^2/g$.

3. The catalyst as claimed in claim 1, which contains from 5 to 30% by mass of said component having hydrogenation activity, based on the total mass of the reduced catalyst.

4. A process for the catalytic hydrogenation of an ester-containing aldehyde mixture, comprising:
    hydrogenating said ester-containing aldehyde in the presence of a supported catalyst, thereby obtaining at least one alcohol corresponding to said aldehyde,
    wherein said supported catalyst comprises γ-alumina having a BET surface area of from 140 to 350 $m^2/g$ as support material and at least one component having hydrogenation activity and being selected from the group consisting of nickel, cobalt and mixtures thereof.

5. The process as claimed in claim 4, wherein said ester-containing aldehyde mixture is a reaction mixture from the hydroformylation of olefins having 6 to 20 C atoms, said reaction mixture having an ester content of from 3 to 15% by mass, based on the total mass of the reaction mixture.

6. The process as claimed in claim 4, wherein said support material has a BET surface area of from 140 to 250 $m^2/g$.

7. The process as claimed in claim 4, wherein said catalyst comprises from 5 to 30% by mass of said component having hydrogenation activity, based on the total mass of the reduced catalyst.

8. The process as claimed in claim 7, wherein the catalyst contains from 15 to 25% by mass of said component having hydrogenation activity, based on the total mass of the reduced catalyst.

9. The process as claimed in claim 4, wherein the hydrogenation is carried out at a pressure of from 0.5 to 25 MPa.

10. The process as claimed in claim 9, wherein the hydrogenation is carried out at a pressure of from 2 to 3 MPa.

11. The process as claimed in claim 4, wherein the hydrogenation is carried out at a temperature of from 120 to 220° C.

12. The process as claimed in claim 11, wherein the hydrogenation temperature is from 160 to 190° C.

13. The process as claimed in claim 4, wherein the hydrogenation is carried out with addition of water to the ester-containing aldehyde mixture.

14. The process as claimed in claim 4, wherein the hydrogenation is carried out without addition of water to the ester-containing aldehyde mixture.

15. The process as claimed in claim 4, wherein said ester-containing aldehyde mixture is a reaction mixture from the hydroformylation of at least one olefin having 8 to 18 C atoms.

16. The process as claimed in claim 4, wherein said ester-containing aldehyde mixture is a reaction mixture from the hydroformylation of di-n-butene, tri-n-butene, tetra-n-butene or mixtures thereof.

17. the catalyst as claimed in claim 1, consisting essentially of said γ-alumina, and said at least one component having hydrogenation activity.

18. The catalyst as claimed in claim 1, consisting of said γ-alumina, and said at least one component having hydrogenation activity.

19. The process as claimed in claim 4, wherein said catalyst consists essentially of said γ-alumina, and said at least one component having hydrogenation activity.

20. The process as claimed in claim 4, wherein said catalyst consists of said γ-alumina, and said at least one component having hydrogenation activity.

* * * * *